United States Patent [19]

Zabotto et al.

[11] Patent Number: 4,715,982

[45] Date of Patent: Dec. 29, 1987

[54] COSMETIC COMPOSITION FOR GENTLE CLEANSING, ESPECIALLY FOR REMOVING EYE MAKEUP

[75] Inventors: Arlette Zabotto, Paris; Jean-Claude Contamin, Morangis, both of France

[73] Assignee: L'Oreal, Paris, France

[21] Appl. No.: 925,135

[22] Filed: Oct. 28, 1986

[30] Foreign Application Priority Data

Oct. 31, 1985 [FR] France ................ 85 16193

[51] Int. Cl.$^4$ ................................ C11D 3/32
[52] U.S. Cl. ........................ 252/174.17; 514/846; 252/174.18; 252/106
[58] Field of Search ............. 252/174.17, 174.18, 252/106

[56] References Cited

FOREIGN PATENT DOCUMENTS 0115888 8/1984 European Pat. Off. .
2104379 3/1983 United Kingdom .
2128627 5/1984 United Kingdom .

Primary Examiner—Paul Lieberman
Assistant Examiner—John F. McNally
Attorney, Agent, or Firm—Cushman, Darby & Cushman

[57] ABSTRACT

A cosmetic composition comprising from 0.2 to 6% by weight of at least one nonionic surface-active agent of formula (I)

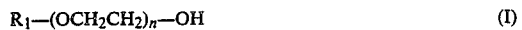

$$R_1-(OCH_2CH_2)_n-OH \quad (I)$$

or (II)

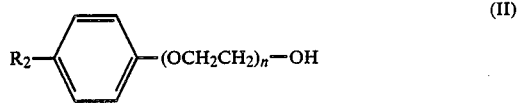

wherein
$R_1$ is a $C_8-C_{18}$ fatty chain;
$R_2$ is a $C_8-C_{16}$ alkyl; and
n is from 10 to 40;

and from 0.02 to 10% by weight of at least one nonionic polymer which is a poly-$\beta$-alanine, alkyl or hydroxyalkyl cellulose, or hydroxypropylated derivative of guar gum, has low irritant behavior towards the skin.

11 Claims, No Drawings

COSMETIC COMPOSITION FOR GENTLE CLEANSING, ESPECIALLY FOR REMOVING EYE MAKEUP

The present invention relates to a cosmetic composition for gentle cleansing, especially a lotion for removing eye makeup, which is remarkable in its markedly low irritant behaviour towards the skin.

French Patent Application No. 2,534,270 discloses a composition for gentle cleansing containing, firstly, as a cleansing agent, at least one nonionic surface-active agent chosen from specific glucoside alkyl ethers, oxyethylenated methylglucoside dioleate and specific alkyland hydroxyalkyl- polyglycosides and, secondly, at least one nonionic polymer which is chosen from alkyl celluloses, polyhydroxyalkyl celluloses, poly-$\beta$-alanines and polyvinylpyrrolidone, whose presence has the effect of, on the one hand, improving the detergency of the surfactant(s) and, on the other hand, reducing the irritancy of the composition towards the skin.

The Applicant has found, completely unexpectedly, that when nonionic surface-active agents consisting of polyglycol ethers of fatty alcohols and/or of and/or of alkylphenols are used instead of the nonionic surface-active agents defined in the abovementioned patent application, the innocuousness of the cosmetic compositions is considerably improved, while very good make-up-removal properties are retained.

The subject of the present invention is therefore the novel industrial product consisting of a cosmetic composition for gentle cleansing, especially for removing eye makeup, characterized in that it contains, in a cosmetically acceptable medium:

(1) from 0.2 to 3% by weight of active substance of at least one nonionic surface-active agent taken from the group consisting of:

the compounds of formula (I):

$$R_1-(OCH_2CH_2)_n-OH \quad (I)$$

in which formula:
$R_1$ denotes a fatty chain containing from 8 to 18 carbon atoms; and
n is a number from 8 to 25; and the compounds of formula (II):

$$R_2-\underset{}{\bigcirc}-(OCH_2CH_2)_n-OH \quad (II)$$

in which formula:
$R_2$ denotes a $C_8-C_{16}$ alkyl residue; and
n is a number from 10 to 40; and (2) from 0.02 to 10% by weight of at least one nonionic polymer taken from the group consisting of poly-$\beta$-alanines, ($C_1-C_3$)alkyl celluloses and hydroxy($C_1-C_3$)alkyl celluloses, and hydroxypropylated derivatives of guar gum;

the above percentages being calculated based on the total weight of the composition.

In accordance with a preferred embodiment of the present invention, the composition contains:
from 0.5 to 3% by weight of active substance of the nonionic surface-active agent(s); and
from 0.05 to 3% by weight of the nonionic polymer(s).

Preferably, in formula (I) $R_1$ denotes a $C_{10}-C_{14}$ fatty chain and, in formula (II), $R_2$ denotes a $C_8-C_{10}$-alkyl residue, while n in the said formulae (I) and (II) preferably denotes a number from 10 to 25.

Preferably still, the radical $R_1$ is the lauryl radical and $R_2$ is a nonyl radical.

Among the nonionic surface-active agents which may be used, there may be mentioned the compounds of formula (I), in which $R_1$ denotes a lauryl radical and n has the values of 10, 16 and 23 respectively, these compounds being sold by the company CHEM'Y under the trade names "Akyporox®", "RLM 100", "RLM 160" and "RLM 230", respectively, and the compounds of formula (II), in which $R_2$ denotes a nonyl radical and n has the values of 10.5, 15 and 20, these compounds being sold under the trade names "Akyporox NP 105", "NP 150" and "NP 200" respectively.

Among the nonionic polymers which may be used in the compositions according to the invention there may be mentioned, in particular:

(1) the poly-$\beta$-alanines described in Belgian Patent No. 893,738.

These polymers comprise from 50 to 100% of repeat units of the $\beta$-alanine type, corresponding to the following formula:

$$\left[\begin{array}{c} CH-CH-C-N \\ | \quad | \quad \| \quad | \\ R^3 \quad R^2 \quad O \quad R^1 \end{array}\right]\!\!\!- \quad (A)$$

and from 0 to 50% of repeat units of the acrylamide type, corresponding to the following formula:

$$\left[\begin{array}{c} R^2 \\ | \\ CH-C \\ | \quad | \\ R^3 \quad C=O \\ | \\ NHR^1 \end{array}\right] \quad (B)$$

in which formulae:
$R^1$ denotes a hydrogen atom or a radical taken from the group consisting of the following radicals:

$$-CH_2-N\underset{O}{\overset{\diagup}{\diagdown\!\!\!\!/}} \quad (i)$$

$-CH_2OH$ (ii)

$-(CH_2)_p-CH_3$, p being 0 or an integer from 1 to 11,; (iii)

$$-CH_2-N\!\!\begin{array}{c}\diagup r' \\ \diagdown r''\end{array}, \quad (iv)$$

r' and r'', which are identical or different, independently denoting a hydrogen atom or a $C_1-C_3$ alkyl radical, $-CHOH-COOH$ (v)

$-CH_2SO_3Na$ (vi)

-continued

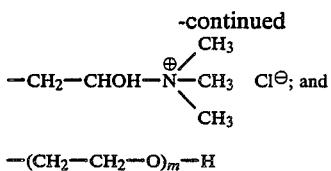

$-(CH_2-CH_2-O)_m-H$ (viii)

m being from 1 to 10; and $R^2$ and $R^3$ denoting a hydrogen atom or a methyl radical.

These polymers are prepared by the polymerization of acrylamide, as described in U.S. Pat. No. 4,082,730; they preferably have a molecular weight from 500 to 200,000 and, more particularly, from 2,000 and 100,000.

(2) $(C_1-C_3)$alkyl celluloses and hydroxy-$(C_1-C_3)$alkyl celluloses having a molecular weight from 60,000 to 1,000,000, the alkyl celluloses being chosen more particularly from methyl and ethyl celluloses, and the hydroxyalkyl celluloses being chosen more particularly from hydroxyethyl, hydroxypropyl methyl celluloses or hydroxypropyl celluloses;

(3) hydroxypropylated derivatives of guar gum, in particular the product sold by the company "Meyhall" under the trade name "Jaguar HP-8".

The vehicle in the cleansing compositions according to the invention is either sterile demineralized water or a "flower" water such as rose water, cornflower water, camomile water or lime-blossom water.

The cleansing compositions according to the present invention may also contain from 0.1 to 5% by weight of active substance of at least one nonionic surface-active agent taken from the group consisting of sorbitol esters of $C_{12}-C_{18}$ fatty acids, polyoxyethylenated with 15–40 moles of ethylene oxide, such as sorbitan monolaurate polyoxyethylenated with 20 moles of ethylene oxide, and $C_{12}-C_{18}$ fatty acids partially esterified with glycerols, polyoxyethylenated with 15 to 40 moles of ethylene oxide, such as glycerol monolaurate polyoxyethylenated with 20 moles of ethylene oxide. The above-mentioned nonionic surface-active agents are known to have low irritancy and, when they are present in the compositions according to the invention, they enable the makeup-removal properties of the latter to be improved further.

The other ingredients of the cleansing compositions according to the invention are essentially a preserving agent, which may be, for example, sodium ethylmercuriothiosalicylate, a chlorhexidine salt such as the digluconate, diacetate and dihydrochloride, a phenylmercury salt such as phenylmercury nitrate, a mixture consisting of 30% by weight of sodium benzoate and 70% by weight of monochloroacetamide, a compound of formula (XII):

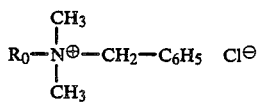

in which:

$R_0$ denotes a $C_{12}-C_{18}$ alkyl radical or a mixture of such alkyl radicals such as the $C_{12}-C_{14}$ and $C_{14}-C_{16}$ mixtures.

The preserving agent in the compositions according to the invention is generally in a concentration of between 0.002 and 0.8% by weight and, preferably, between 0.02 and 0.5% by weight.

The pH of the compositions according to the invention is generally between 6 and 8; it is obtained with the aid of a buffer agent such as, for example, a phosphate buffer (dipotassium hydrogen phosphate/potassium dihydrogen phosphate).

The compositions according to the invention may also contain other conventional adjuvants such as, for example, moistening agents, softening agents, perfumes or colorants, it being necessary for these, of course, to have the characteristic of being stable within the composition and of not causing irritation or smarting of the eye mucosa.

Among the moistening agents there may be mentioned, in particular, 2-methyl-2,4-pentanediol and polyethylene glycol with a molecular weight of approximately 600.

Among the softening agents, there may be mentioned, in particular, allantoin and azulene.

To enable the subject of the invention to be better understood, several embodiments thereof will now be described, by way of purely illustrative examples without implying any limitations.

EXAMPLE 1

A lotion for removing eye makeup, formulated as follows, is prepared:

| | |
|---|---|
| Lauryl alcohol oxyethylenated with 16 moles of ethylene oxide, of formula: $CH_3-(CH_2)_{10}-CH_2-(OCH_2-CH_2)_{16}OH$, sold under the trade name "Akyporox ® RLM 160" by the company "CHEM'Y" | 1 g |
| Poly-$\beta$-alanine prepared according to Example 1 of Belgian Patent No. 893,738 | 0.5 g |
| Allantoin | 0.05 g |
| Potassium dihydrogen phosphate | 0.1 g |
| Potassium hydrogen phosphate | 0.3 g |
| Sodium ethylmercuriothiosalicylate | 0.003 g |
| Perfume | 0.1 g |
| Sterile demineralized water q.s. | 100 g |

This lotion has a pH of approximately 7.

Cotton wool, or a disposable tissue for removing makeup, is impregnated with this lotion and then applied to the eyelids and the eyelashes with a rubbing motion. The makeup is removed satisfactorily in this manner and eye comfort is very good, even when this lotion contacts the eye mucosa.

EXAMPLE 2

A lotion for removing eye makeup, formulated as follows, is prepared:

| | |
|---|---|
| Lauryl alcohol oxyethylenated with 23 moles of ethylene oxide, of formula: $CH_3-(CH_2)_{10}-CH_2-(OCH_2-CH_2)_{23}OH$, sold under the trade name "Akyporox ® RLM 230" by the company "CHEM'Y" | 2 g |
| Hydroxyethyl cellulose sold under the trade name "Natrosol 250" by the "Hercules" company | 0.1 g |
| 2-Methyl-2,4-pentanediol | 2 g |
| Potassium dihydrogen phosphate | 0.1 g |
| Potassium hydrogen phosphate | 0.3 g |
| Mixture of myristyl- and cetyldimethyl-benzylammonium chlorides | 0.1 g |
| Perfume | 0.1 g |
| Sterile demineralized water q.s. | 100 g |

This lotion has a pH of approximately 7.1.

Excellent removal of makeup is obtained, without any irritant effect, by proceeding in an identical manner to that described in Example 1.

EXAMPLE 3

A lotion for removing eye makeup, formulated as follows, is prepared:

Nonyl phenol oxyethylenated with 15 moles of ethylene 5 oxide, of formula:

$$C_9H_{19}-\!\!\!\bigcirc\!\!\!-(O-CH_2CH_2)_{15}OH$$

| | |
|---|---|
| sold under the trade name "Akyporax NP150" by the company "CHEM'Y" | 1 g |
| Poly-β-alanine prepared according to Example 1 of Belgian Patent No. 893,738 | 0.5 g |
| Allantoin | 0.05 g |
| Potassium dihydrogen phosphate | 0.1 g |
| Potassium hydrogen phosphate | 0.3 g |
| Sodium ethylmercuriothiosalicylate | 0.003 g |
| Perfume | 0.1 g |
| Sterile demineralized water q.s. | 100 g |

This lotion has a pH of approximately 7.

Excellent removal of makeup is obtained without any irritant effect, by proceeding in an identical manner to that described in Example 1.

EXAMPLE 4

Demonstration of the absence of irritancy of the cosmetic compositions for gentle cleansing according to the present invention.

(a) Principle of the measurement of irritancy of a cosmetic composition

It is known that detergents have the effect of causing the haemolysis of red blood corpuscles. In fact, a suspension of red blood corpuscles forms a turbidity which absorbs light of all wavelengths and, in particular, at 540 nm, and the lysed red blood corpuscles release, in the incubation medium, their haemoglobin, which absorbs at a wavelength of 540 nm. When lysing the red blood corpuscles, detergents therefore cause the disappearance of the turbidity due to the latter and, after centrifuging (800 g/15 min) produce a supernatant which is clear and coloured by the haemoglobin. To measure the irritancy of a cleansing composition, a determination is made of the concentration of the said composition in physiological saline solution, at which 50% lysis of the red blood corpuscles is produced. This concentration is called the semi-lysis point of the cleansing composition. The higher the semi-lysis point of a cleansing composition, the lower the irritancy of this composition.

(b) General operating procedure for this measurement

Rat blood is collected by removal onto 0.06% strength heparin in physiological saline solution (0.15 M NaCl), from the aorta of the animal, anaesthetized with ether before-hand. Separation of the red blood corpuscles from the saline solution is produced by centrifuging 500 g/15 min, with repeated washing using the heparin-containing medium until a clear supernatant is obtained. The red blood corpuscles are then washed twice with physiological saline solution to remove the heparin. The last centrifuging residue is resuspended in physiological saline solution at a concentration of $4 \cdot 10^4$ cells per cubic millimeter.

One milliliter of red blood corpuscles, i.e. $4 \cdot 10^7$ cells, is incubated for 10 minutes in the presence of various concentrations of cleansing compositions, diluted or dissolved beforehand in physiological saline solution. After incubation, the optical density of the incubation medium is read off at 540 nm, and then the incubate is centrifuged at 800 g for 10 min and the optical density of the supernatant is read off at 540 nm. The residue of unlysed red blood corpuscles is resuspended in 1 ml of physiological saline solution and the cells are counted in a Mallasvez cell.

(c) Result

The semi-lysis point has been calculated as a percentage of lotion for five lotions for removing eye makeup, lotions Nos. 1 to 3 being those in the abovementioned Examples 1 to 3, respectively, lotion No. 4, containing a known nonionic surface-active agent (Triton CG-110, sold by the Rohm & Haas company), and lotion No. 5 being strictly identical to lotion No. 4, except that the known surface-active agent is replaced by a surface-active agent according to the invention, namely that of Example 2.

The formulations No. 1 to No. 5, and the corresponding semi-lysis points are given in the table below:

TABLE

| Lotion formulation | 1 | 2 | 3 | 4 | 5 |
|---|---|---|---|---|---|
| Surfactants | | | | | |
| Surface-active agent of Example 1 | 1 g | | | | |
| Surface-active agent of Example 2 | | 2 g | | | 0.4 g |
| Surface-active agent of Example 3 | | | 1 g | | |
| Known* surface-active agent | | | | 0.66 g (i.e. 0.4 g of active substance) | |
| Polymer | | | | | |
| Poly-β-alanine | 0.5 g | | 0.5 g | 0.5 g | 0.5 g |
| Hydroxyethyl cellulose | | 0.1 g | | | |
| Softening agent | | | | | |
| Allantoin | 0.05 g | | 0.05 g | | |
| Moistening agent | | | | | |
| 2-Methyl-2,4-pentanediol | | 2 g | | 1 g | 1 g |
| Phosphate buffer | | | | | |
| Potassium dihydrogen phosphate | 0.1 g | 0.1 g | 0.1 g | 0.1 g | 0.1 g |

TABLE-continued

| Lotion formulation | 1 | 2 | 3 | 4 | 5 |
|---|---|---|---|---|---|
| Potassium hydrogen phosphate | 0.3 g | 0.3 g | 0.3 g | 0.3 g | 0.3 g |
| Preserving agent | | | | | |
| Potassium ethylmercuriothio-salicylate | 0.003 g | | 0.003 g | 0.003 g | 0.003 g |
| Mixture of myristyl- and cetyl-dimethylbenzylammonium chlorides | | 0.1 g | | | |
| Perfume | 0.1 g | 0.1 g | 0.1 g | 0.1 g | 0.1 g |
| Water q.s. | 100 g | 100 g | 100 g | 100 g | 100 g |
| Semi-lysis point as percentage of lotion | 27.5 | 35 | >50 | 25.75 | >50 |
| EI (eye irritation) | 7.33 (1 h) 1.00 (D 2) | 9.33 (1 h) 0.67 (D 2) | | 3.00 (1 h) 2.67 (D 1) | 1.67 (1 h) 0.67 (D 1) |

The known surface-active agent referred to in the fourth line of the preceding table and marked with the symbol * is a composition sold under the trade name "Triton CG-110" by the "Rohm & Haas" company and containing, as nonionic surface-active agent, a glucoside alkyl ether of formula:

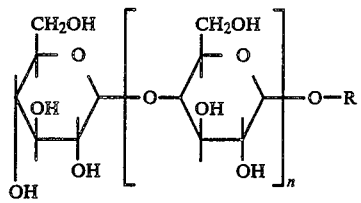

in which R denotes a $C_8$-$C_{10}$ (50/50) radical and n has a mean value of approximately 3.

It is found that formulation No. 5, which differs from formulation No. 4 only in the nature of the surfactant, has a semi-lysis value higher than 50% of lotion, whereas formulation No. 4 has a semi-lysis point of 25.75% of lotion. It follows from this that formulation No. 5 may be considered as being half as irritant as composition No. 4.

It is found, furthermore, that formulations No. 1 and No. 2, which have a higher concentration of surface-active agent than composition No. 4 have nevertheless a semi-lysis point which is higher than that of this formulation No. 4.

It is noted that formulation No. 3 may be considered as being half as irritant as composition No. 4, even though it has a higher concentration of surface-active agent.

The results of the eye irritation test are calculated on the basis of the preceding table. These tests were carried out, in a conventional manner, on rabbits' eyes (Draize test) and the irritation indices (EI) were determined according to the specifications published in the Journal Officiel in this connection. It is known that an EI value lower than or equal to 5 corresponds to nonirritancy; when the EI value is between 5 and 15, the formulation has a markedly low irritant capacity. In the table, the indications shown in parentheses in the case of the values of the EI indices indicate the time when the inspection was carried out. The symbol (1 h) means that the inspection was carried out after 1 hour; the symbol (D 1) means that the inspection was carried out after 1 day; the symbol (D 2) means that the inspection was carried out after 2 days. If the IE value after 1 hour of composition No. 5 according to the invention and of composition No. 4 of the state of the art are compared, it is found that, although the concentration of surfactant is comparable in both compositions, formulation No. 5 is half as irritant as formulation No. 4.

We claim:

1. A cosmetic composition suitable for gentle cleansing which comprises:
    (1) from 0.2 to 3% by weight of at least one active substance which is a nonionic surface-active agent which is a compound of formula (I):

$$R_1-(OCH_2CH_2)_n-OH$$

wherein $R_1$ is a fatty chain containing from 8 to 18 carbon atoms and n is from 8 to 25, or a compound of formula (II):

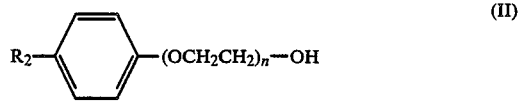

wherein
    $R_2$ is a $C_8$-$C_{16}$ alkyl residue and
    n is from 10 to 40;
    (2) from 0.02 to 10% by weight of at least one nonionic polymer which is a poly-$\beta$ alanine, a $C_1$-$C_3$ alkyl cellulose, a hydroxy $C_1$-$C_3$ alkyl cellulose or a hydroxypropylated derivative of guar gum; and a cosmetically acceptable adjuvant, the above percentages being based on the total weight of the composition.

2. A composition according to claim 1, which comprises:
    from 0.5 to 3% by weight of nonionic surface-active agent; and
    from 0.05 to 3% by weight of nonionic polymer.

3. A composition according to claim 1 wherein, in formula (I), $R_1$ is a $C_{10}$-$C_{14}$ fatty chain, and, in formula (II), $R_2$ is a $C_8$-$C_{10}$ alkyl radical and n, in either of formulae (I) or (II), is a number from 10 to 25.

4. A composition according to claim 3, wherein $R_1$ is a lauryl radical or $R_2$ is a nonyl radical.

5. A composition according to claim 3, wherein, in formula (I), $R_1$ is a lauryl radical and n is 10, 16 or 23.

6. A composition according to claim 1 wherein the poly-$\beta$-alanine is a polymer comprising:
    from 50 to 100% of repeat units of the $\beta$-alanine type of formula (A):

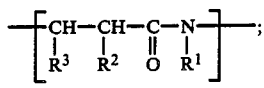 (A)

and from 0 to 50% of repeat units of the acrylamide type of formula (B):

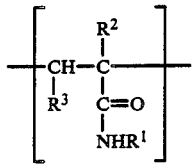 (B)

wherein $R^1$ is a hydrogen atom;

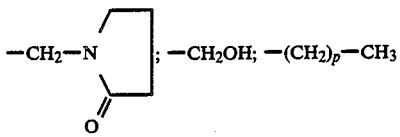

wherein p is 0 or an integer from 1 to 11;

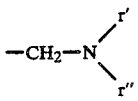

wherein r' and r", which are identical or different, are a hydrogen atom or a $C_1-C_3$ alkyl radical;

—CHOH—COOH; —CH$_2$SO$_3$Na;

-continued

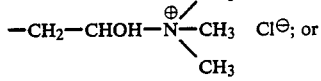

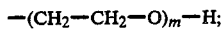

wherein m is from 1 to 10; and $R^2$ and $R^3$, which are identical or different, are a hydrogen atom or a methyl radical.

7. A composition according to claim 1 wherein the $C_1-C_3$ alkyl cellulose or hydroxy $C_1-C_3$ alkyl cellulose has a molecular weight of from 60,000 to 1,000,000.

8. A composition according to claim 1 which has a pH of from 6 to 8.

9. A composition according to claim 1 which additionally comprises, as active substance, from 0.1 to 5% by weight of at least one nonionic surface-active agent which is a sorbitol ester of a $C_{12}-C_{18}$ fatty acid which is polyoxyethylenated with 15-40 moles ethylene oxide or a $C_{12}-C_{18}$ fatty acid partially esterified with glycerol, which is polyoxyethylenated with 15-40 moles ethylene oxide.

10. A composition according to claim 1 which additionally comprises from 0.002 to 0.8% by weight of at least one preserving agent which is sodium ethylmercuriothiosalicylate, a chlorhexidine salt, a phenylmercury salt, a mixture comprising 30% by weight sodium benzoate and 70% by weight monochloroacetamide, or a compound of formula:

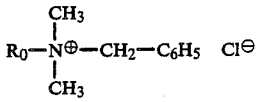

in which $R_0$ is a $C_{12}-C_{18}$ alkyl radical, a mixture of such alkyl radicals, a mixture of $C_{12}-C_{14}$ radicals or a mixture of $C_{14}-C_{16}$ radicals.

11. A composition according to claim 1 which additionally comprises at least one moistening agent, softening agent, perfume or colorant.

* * * * *